US 10,806,469 B2

(12) United States Patent
Fiechter et al.

(10) Patent No.: US 10,806,469 B2
(45) Date of Patent: Oct. 20, 2020

(54) PATIENT-SPECIFIC NAVIGATIONAL GUIDE

(71) Applicant: MEDACTA INTERNATIONAL SA, Castel San Pietro (CH)

(72) Inventors: Meinrad Fiechter, Lugano (CH); Alberto Lipari, Civate (IT); Francesco Siccardi, Castel san Pietro (CH)

(73) Assignee: Medacta International SA, Castel San Pietro (CH)

( * ) Notice: Subject to any disclaimer, the term of this patent is extended or adjusted under 35 U.S.C. 154(b) by 180 days.

(21) Appl. No.: 15/526,533

(22) PCT Filed: Oct. 30, 2015

(86) PCT No.: PCT/IB2015/058399
§ 371 (c)(1),
(2) Date: May 12, 2017

(87) PCT Pub. No.: WO2016/075581
PCT Pub. Date: May 19, 2016

(65) Prior Publication Data
US 2017/0311960 A1 Nov. 2, 2017

(30) Foreign Application Priority Data
Nov. 14, 2014 (IT) .............................. MI2014A1969

(51) Int. Cl.
A61B 17/17 (2006.01)
A61B 17/56 (2006.01)
(Continued)

(52) U.S. Cl.
CPC .......... *A61B 17/1757* (2013.01); *A61B 17/56* (2013.01); *A61B 17/1796* (2013.01);
(Continued)

(58) Field of Classification Search
CPC ............ A61B 17/1757; A61B 17/1796; A61B 17/1739; A61B 17/17; A61B 17/7076
See application file for complete search history.

(56) References Cited

U.S. PATENT DOCUMENTS 5,928,232 A * 7/1999 Howland ........... A61B 17/7001
606/276
2011/0319745 A1* 12/2011 Frey ....................... A61B 17/15
600/407
(Continued)

FOREIGN PATENT DOCUMENTS

EP 2749235 A1 7/2014
TW 201238556 A 10/2012
(Continued)

OTHER PUBLICATIONS

International Search Report and Written Opinion dated Jan. 20, 2016 from International Application No. PCT/IB2015/058399, 11 pages.
(Continued)

Primary Examiner — Amy R Sipp
(74) Attorney, Agent, or Firm — Meunier Carlin & Curfman LLC

(57) ABSTRACT

A patient-specific navigational guide (1, 1') for use in spinal surgery, comprises two tubular guiding member (2) extending from a proximal opening (2a) and a distal opening (2b) for guiding a surgical operation on a patient's vertebra (100, 100'). The two tubular guiding members are integral with a bearing frame (3) comprising at least five contact members (11, 15, 16) designed to match with a corresponding plurality of contact areas on the patient's vertebra (100, 100') in order to define a unique coupling configuration of the patient-specific navigational guide (1, 1') on the patient's vertebra (100, 100'). The contact members (11, 15, 16) comprise a main contact member (11), designed to couple
(Continued)

with a main contact area corresponding to the spinous process (101) of the patient's vertebra (100, 100') in said coupling configuration, and at least one pair of first and second auxiliary contact members (15, 16), designed to abut on auxiliary contact areas, respectively corresponding to the laminae (102) of the patient's vertebra (100) and to the facet (103) or to the transverse processes (104), in said coupling configuration. The bearing frame (3) comprises a V-shaped bridge (5), connecting the two tubular guiding members (2) and a non-rectilinear bridge (8) further connecting the two tubular guiding members (2) at proximal portions of the tubular guiding members (2), near the proximal openings (2a), and comprises at least one summit portion (8a) defining the more proximal portion of the navigational guide (1).

14 Claims, 6 Drawing Sheets

(51) Int. Cl.
  *A61B 17/88* (2006.01)
  *A61B 17/84* (2006.01)

(52) U.S. Cl.
  CPC ......... *A61B 17/848* (2013.01); *A61B 17/8897* (2013.01); *A61B 2017/568* (2013.01)

(56) References Cited

U.S. PATENT DOCUMENTS

| | | | |
|---|---|---|---|
| 2013/0123850 A1* | 5/2013 | Schoenefeld | A61B 17/1757 606/248 |
| 2013/0218163 A1* | 8/2013 | Frey | A61B 5/0488 606/87 |
| 2014/0358152 A1* | 12/2014 | Condino | A61B 17/1757 606/96 |

FOREIGN PATENT DOCUMENTS

| | | |
|---|---|---|
| WO | 2014070889 A1 | 5/2014 |
| WO | 2014090908 A1 | 6/2014 |
| WO | 2014197844 A1 | 12/2014 |

OTHER PUBLICATIONS

International Search Report and Written Opinion dated Feb. 5, 2016, from International Application No. PCT/IB2015/058772, 12 pages.

* cited by examiner

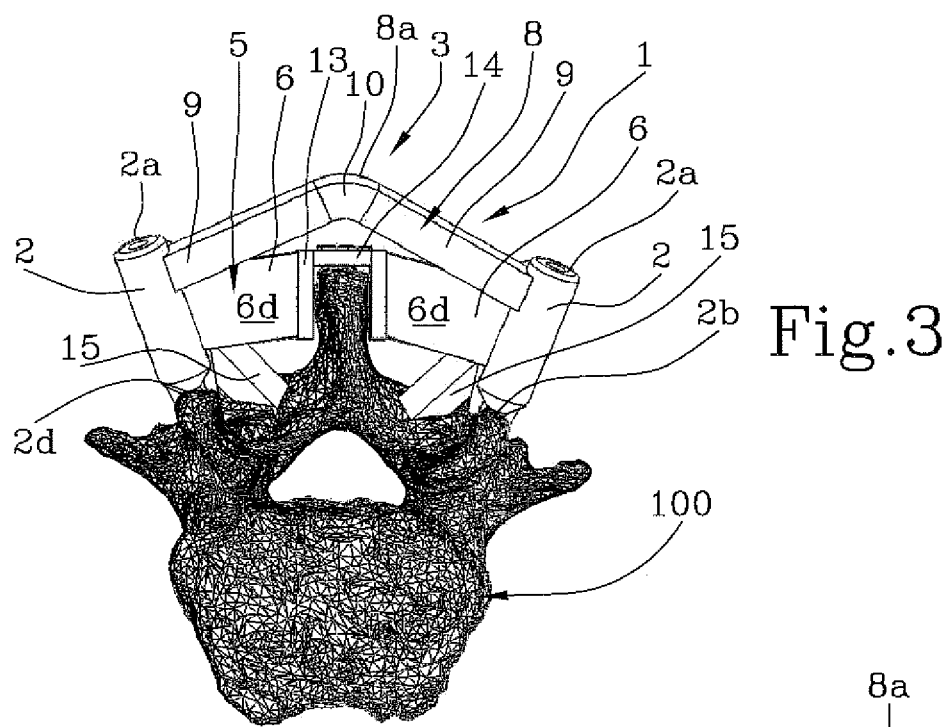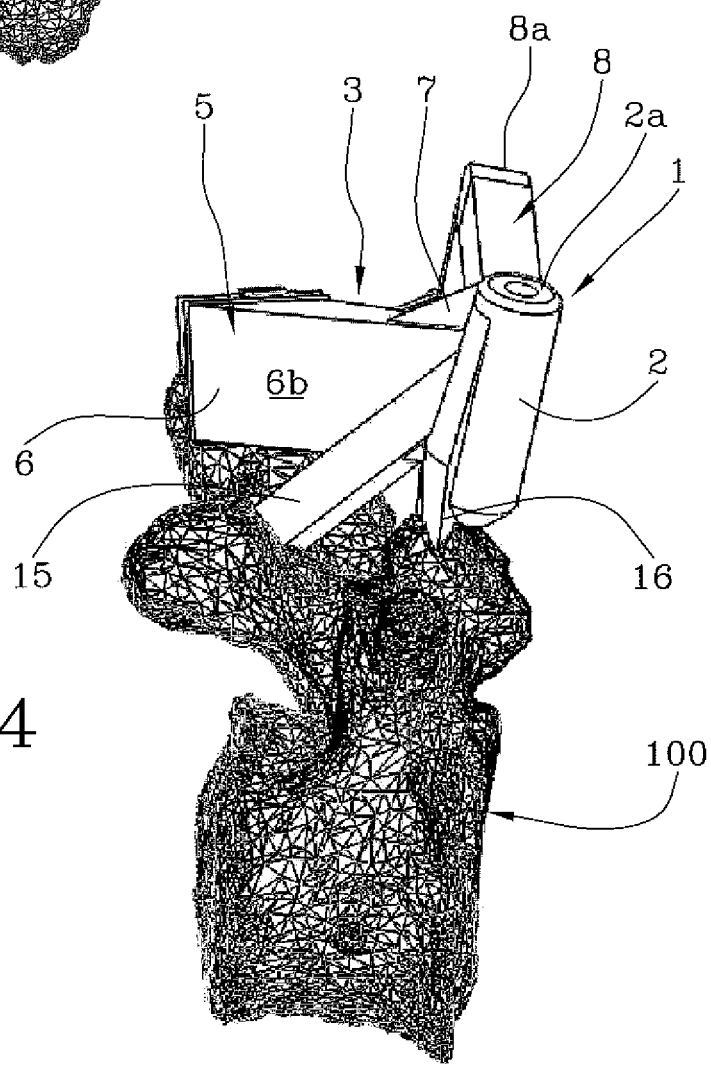

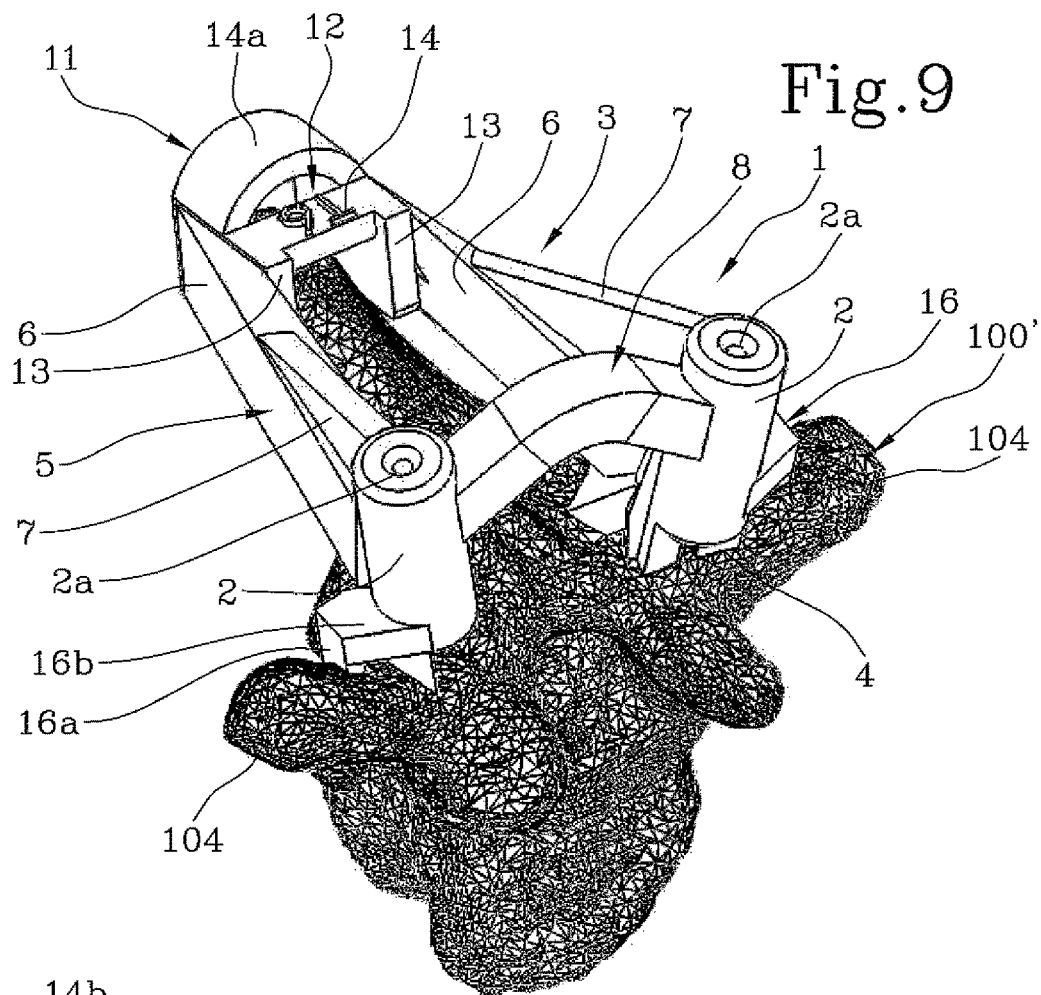
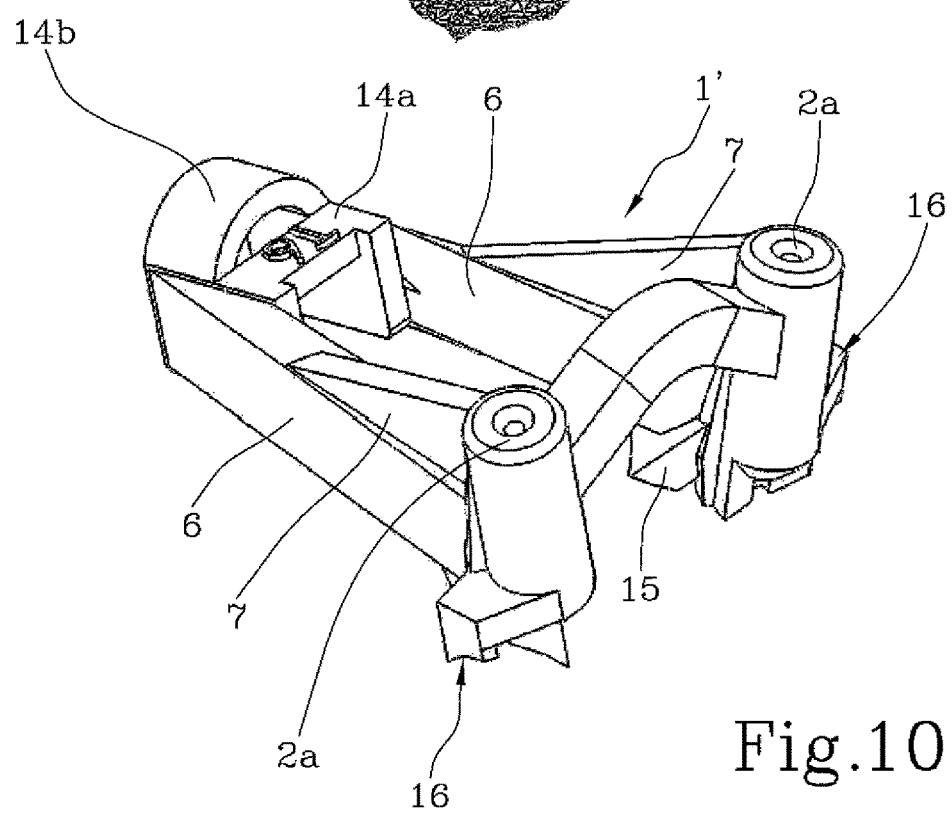

PATIENT-SPECIFIC NAVIGATIONAL GUIDE

The present invention relates to the technical field of orthopedic surgery. More specifically, the invention relates to a patient-specific navigational guide for the spine to be employed in spinal surgery.

Patient-specific guides are disposable templates, which are individually designed to match the bone anatomy derived from CT-scans of a given patient. Surgical operations like drills and cuts can be pre-operatively planned by computer-aided technologies, and the resulting patient-specific guides will later allow the surgeon to accurately replicate the planned operations on the patient's body.

Patient-specific guides have been employed in several fields of orthopedic surgery, including spinal surgery.

In this field, patient-specific guides are mainly employed to help the surgeon during pedicle screw insertion, so that the screw can be inserted according to a pre-planned optimal screw axis.

However, patient-specific guides may be used in spinal surgery for other purposes; for instance as cutting guides during PSO (Pedicle substraction osteotomies), laminotomy or facectomies.

The guides have to be designed in such a way that they couple with the patient's vertebrae in a stable and well-defined configuration. In order to achieve this goal, it is necessary to have large contact areas between the guide and the bony structure of the patient.

Therefore, before the positioning of the guide, the surgeon is forced to clean a large area of the bone from the surrounding tissue, and in some cases to severe the ligaments. This often proves to be a difficult and time-consuming task, and may lead to complication and lengthening of the patient recovery.

Moreover, the remaining tissue that the surgeon is unable to remove may lead to slippery and deviation of the guide, eventually resulting in an incorrect or suboptimal positioning of the pedicle screws or bone resections.

In view of the foregoing, the technical problem underlying the present invention is to provide a patient-specific surgical guide, of the type being used in spinal surgery, which stably and uniquely couples with the vertebrae of a patient without resorting to large contact areas.

The above-mentioned technical problem is solved by a patient-specific navigational guide for use in spinal surgery, according to claim 1.

The invention provides for an improved stability by means of at least five contact points and a specific additional bridging element. This creates a stable construct even in case of one contact area is damaged during the surgery.

The patient-specific navigational guide according to the invention has a low profile guide, which is preferably used to place a guide wire into the vertebrae.

The non-rectilinear bridge makes the guide stable regarding medial lateral deformation at the position of the wire/screw entry point. The known guides have the risk of deformation which cause a deviation between the planned and actual screw position. The screw can be wrong positioned and can sever damage to the neural structure for these kind of applications.

The guide according to the present invention is suitable for Cervical, Thoracic, Lumbar spine and sacrum.

Further features and advantages of the patient-specific navigational guide according to the invention shall be made clearer by the description, given herein below, of a number of embodiments described by way of non-limiting example with reference to the accompanying drawings.

FIGS. 1-4 show perspective views of a first embodiment of the patient-specific navigational guide according to the invention, coupled to a lumbar vertebra;

FIGS. 8-9 show perspective views of second embodiment of the patient-specific navigational guide according to the invention, coupled to a thoracic vertebra;

FIGS. 10-12 show perspective views of the second embodiment of the patient-specific navigational guide according to the invention.

Figure 1:
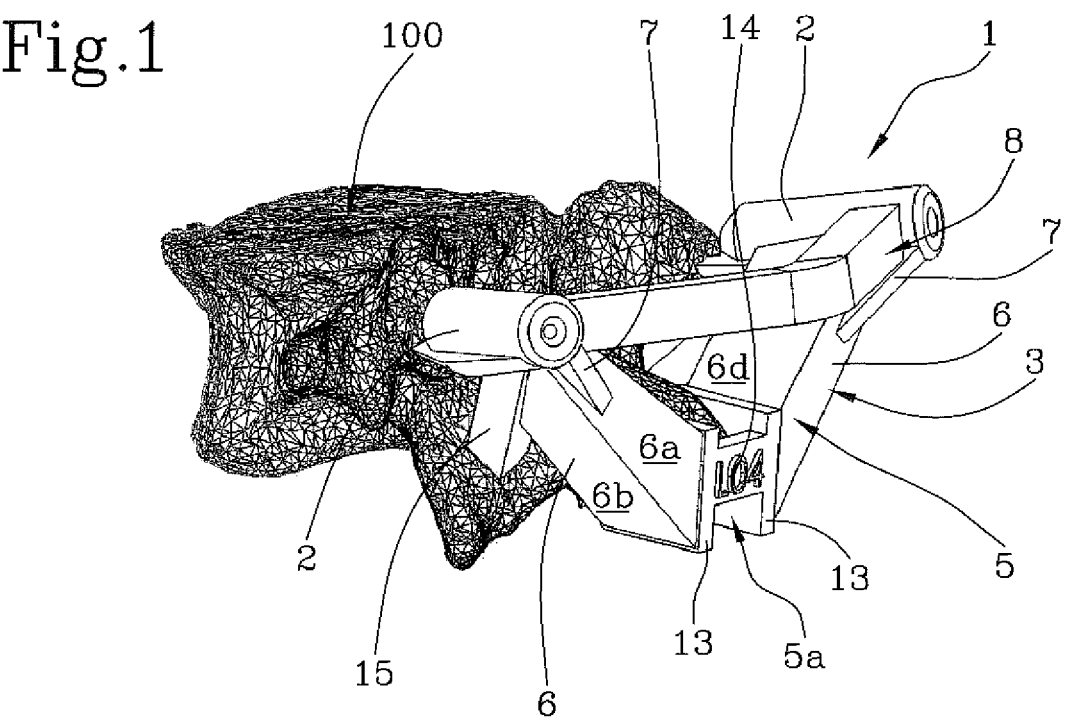
Figure 2:
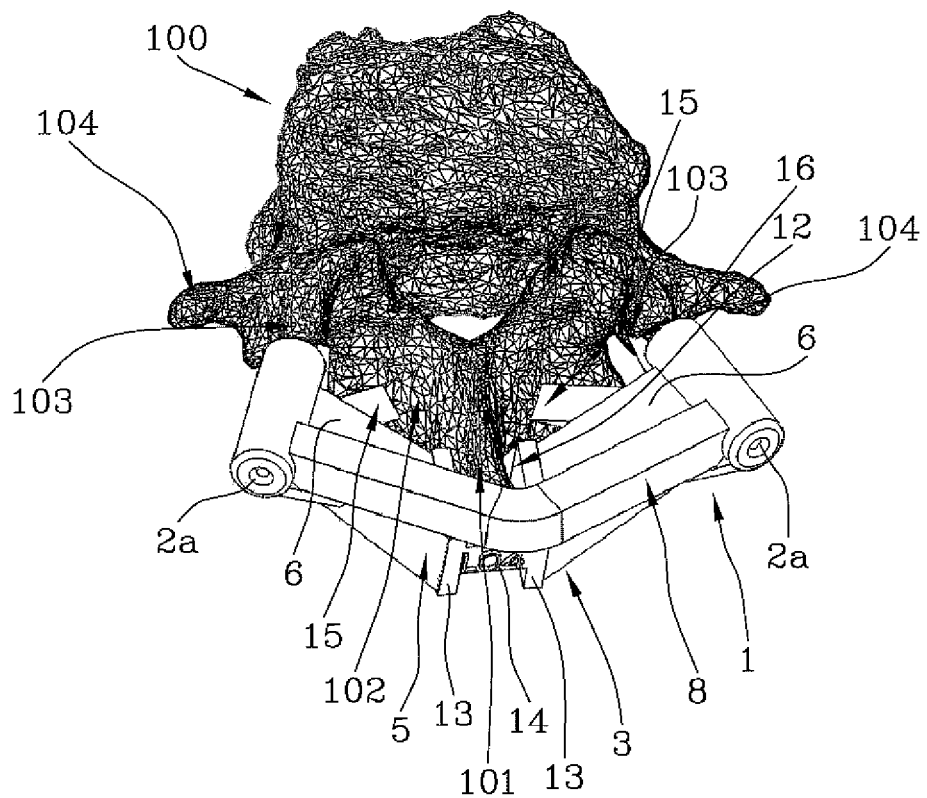
Figure 5:
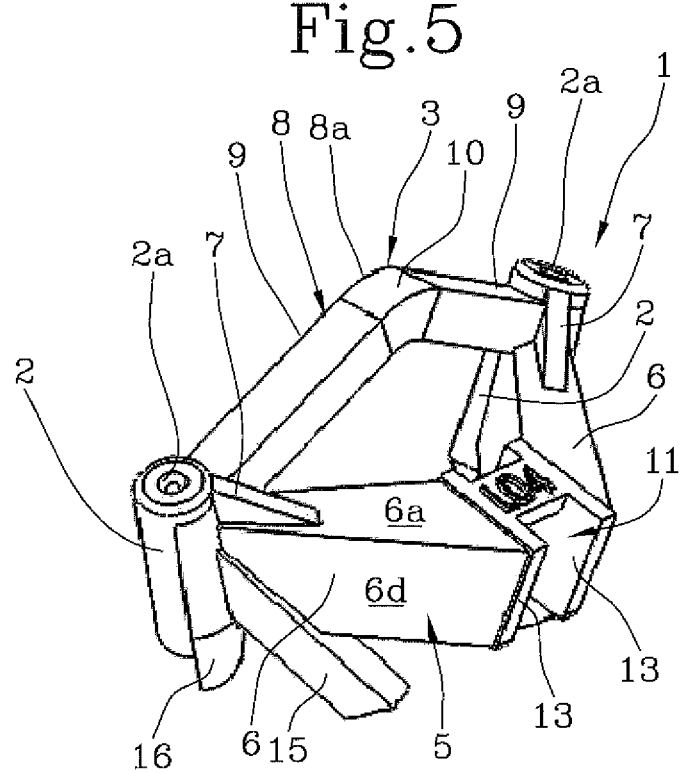
FIGS. 5-7 show perspective views of the first embodiment of the patient-specific navigational guide according to the invention.
Figure 6:
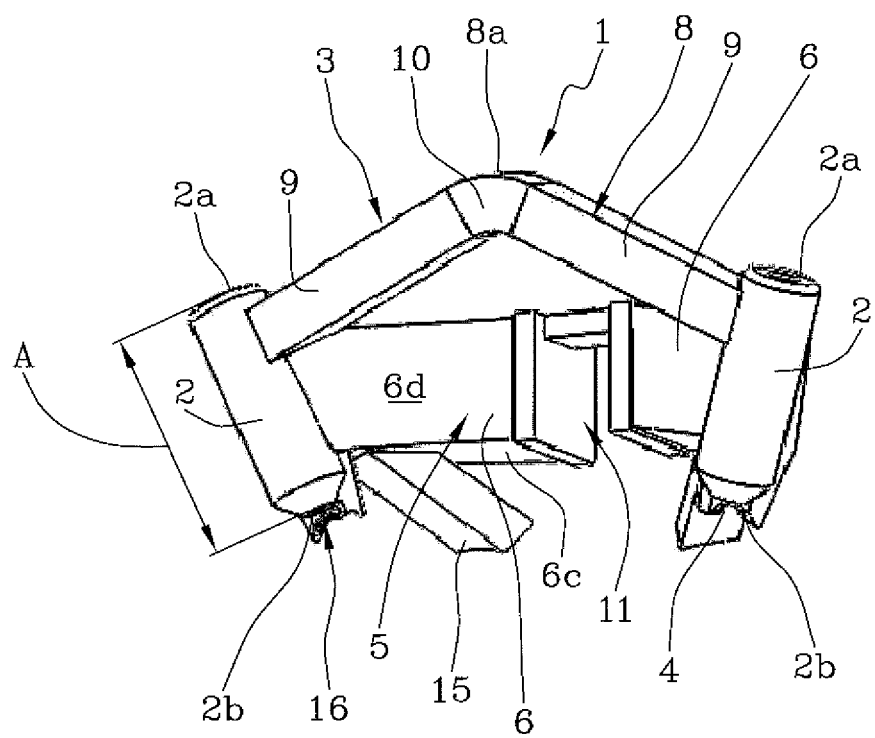
Figure 7:
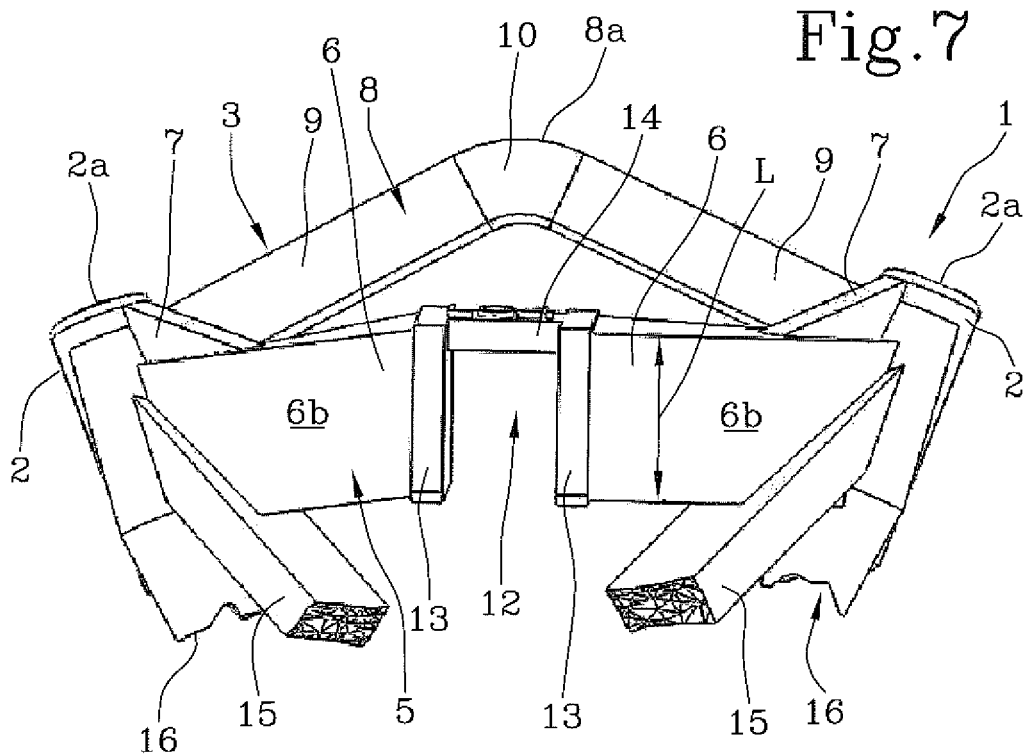

Referring to FIGS. 1-7, a first embodiment of a patient-specific navigational guide 1 for spinal surgery is illustrated, which is specifically designed for operations on a lumbar vertebra 100.

As may be readily recognized in these figures, the navigational guide 1 comprises two tubular guiding members 2.

The two tubular guiding members are integral with a bearing frame 3.

The two tubular guiding members 2 define the insertion axes for two pedicle screws, which should be inserted in the lumbar vertebra according to a pre-operatively planned angle. The insertion axes corresponds to the longitudinal axes of the tubular guiding members 2. Therefore, the tubular guiding members 2 feature an proximal opening 2a, wherefrom a surgical tool could be inserted, and a distal opening 2b in the vicinity of the patient's vertebra. The terms "proximal" and "distal" are used with reference to the surgeon.

The inner diameter of the tubular guiding members 2 is such as to allow the insertion of a Kirchner wire. The Kirchner wire is implanted in the bone and, when the guide 1 is removed, is used to guide a polyaxial screw which runs along the K-wire in order to touch the bone and be implanted.

The inner diameter of the tubular guiding members 2 can be large enough to allow passage of a polyaxial screw. The inner diameter of the tubular guiding members 2 can be selected from 3-18 mm, 3-12 mm, 3-9 mm, 3-6 mm.

The distal opening 2b can comprise a gate 4 forming an open window so that the surgeon can check the entry point of the pedicle screw or Kirchner wire inserted through the tubular guiding members 2.

The bearing frame 3 comprises a V-shaped bridge 5, connecting the two tubular guiding members 2.

The V-shaped bridge 5 has two arms 6: each arm 6 is connected to a tubular guiding member 2 and points toward the caudal direction, so that a vertex 5a of the V-shaped bridge 5 is positioned above the spinous process 101 of the lumbar vertebra 100.

Each of the two arms 6 has a prismatic shape defined by planar surfaces 6a-6d. The prismatic shape of the arms 6 enlarges from the tubular guiding member 2 to the vertex 5a. In particular each arm 6 comprises a proximal surface 6a and a distal surface 6c, each having a substantially triangular shape, and two opposite planar surfaces 6b, 6d, each having a substantially rectangular shape.

The V-shaped bridge 5, in particular each arm 6, connects the two tubular guiding members 2 at a substantially central portion of each tubular guiding members 2, between the proximal opening 2a and the distal opening 2b.

In particular, the width L of the two opposite planar surfaces 6b and 6d of each arm 6 of the V-shaped bridge 5 defines an extended connecting portion between the tubular guiding members 2 and the V-shaped bridge 5. Preferably, the width L is greater than A/2, in which A is the distance between the proximal opening 2a and the distal opening 2b.

Reinforcing ribs 7 can be provided to connect the arms 6 of the V-shaped bridge 5 to the tubular guiding members 2. In particular, each rib 7 extends from a portion near the proximal opening 2a to the proximal surface 6a of each arm 6.

A non-rectilinear bridge 8 further connects the two tubular guiding members 2. In particular the non-rectilinear bridge 8 connects proximal portions of the tubular guiding members 2, near the proximal openings 2a, and comprises at least one summit portion 8a defining the more proximal portion of the navigational guide 1.

Considering an inner volume defined by the two tubular guiding elements 2 and the V-shaped bridge 5, the non-rectilinear bridge 8 extends from the proximal portions of the tubular guiding members 2 towards the outside.

Preferably, the non-rectilinear bridge 8 comprises two arms 9, preferably two rectilinear arms 9, connected by a curved portion 10 defining the summit portion 8a.

Figure 8:
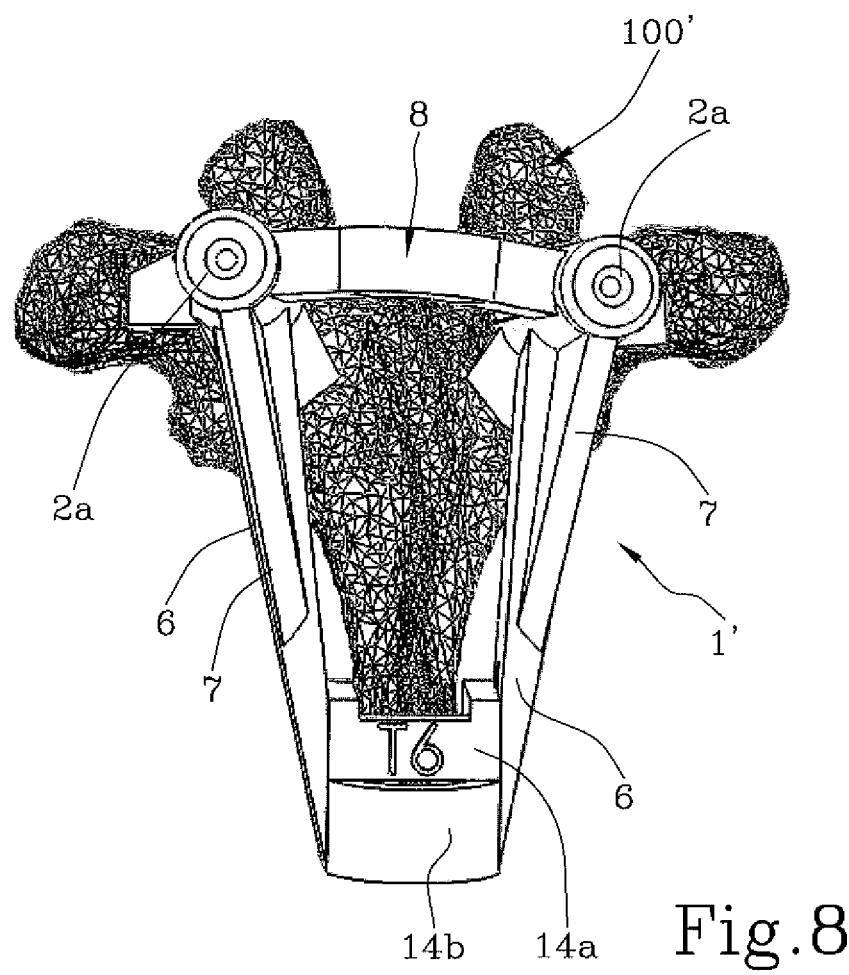
Figure 11:
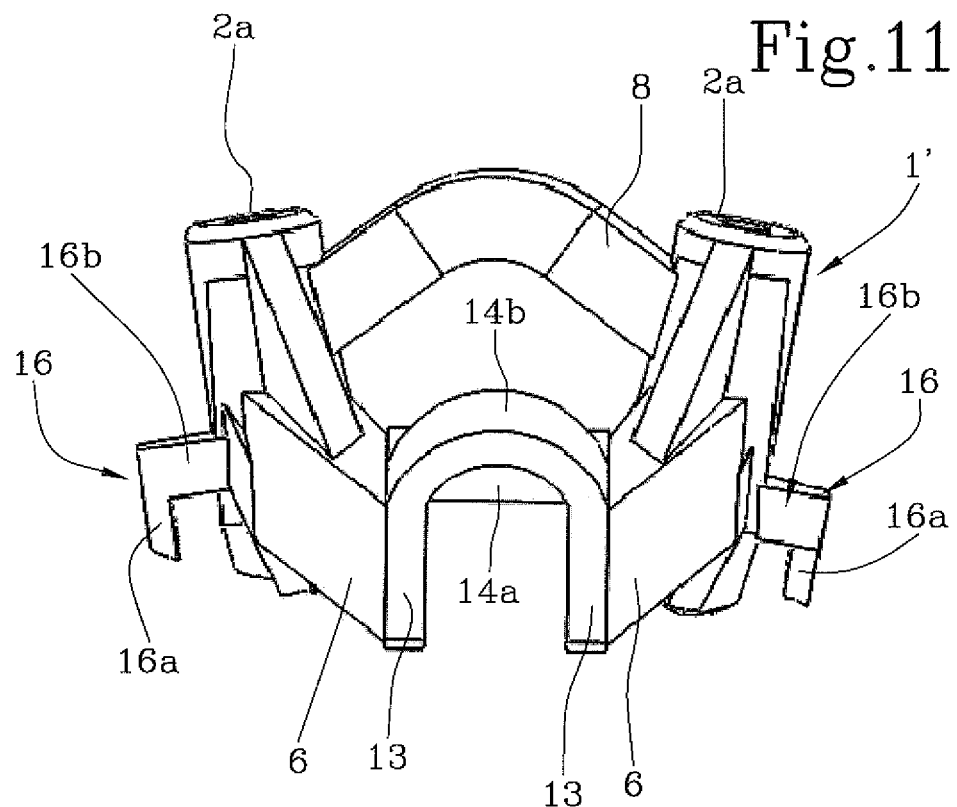
Figure 12:
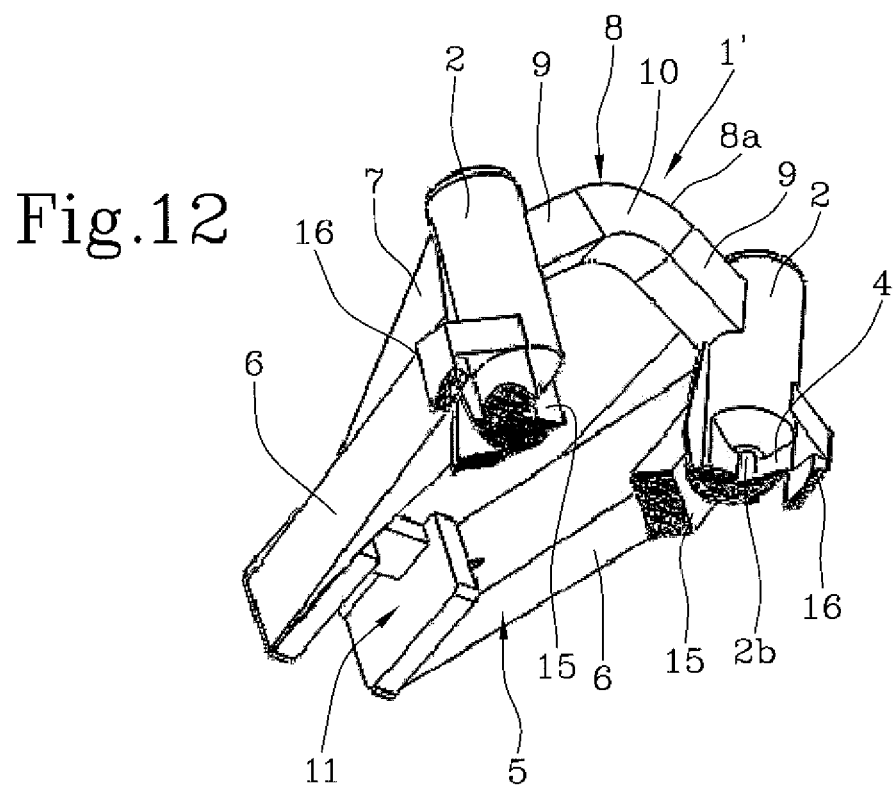

Preferably, the non-rectilinear bridge 8 remains within a theoretical plane comprising the two tubular guiding members 2. In particular, considering the guide 1 in a plan view (like FIG. 8), the non-rectilinear bridge 8 with its summit portion 8a lie on a plane comprising the longitudinal axes of the tubular guiding members 2. This arrangement allows to improve stability of the guide 1. Indeed this arrangement prevent any flexion of the guide (that is that the two tubular guiding members 2 cannot be approach one to the other) and guarantees the accuracy for K-Wire/screw placement. Therefore the guide 1 allows to avoid errors (due to elastic deformation of the bridge 8) when the K-Wire/screw is positioned.

The non-rectilinear bridge 8 and the V-shaped bridge 5 can be arranged to form an angle of at least 90° between the theoretical plate comprising the non-rectilinear bridge 8 and two tubular guiding members 2 and the theoretical plate comprising the V-shaped bridge 5.

The pre-operatively planning is performed, by means of computer-aided design tools, on a three-dimensional model of the bony structure developed from a three-dimensional image (e.g. CT/MRI scan) of the patient. Therefore, the navigational guide 1 is designed in such a way that it uniquely matches the bony structure of the patient.

In particular, to ensure a correct and stable positioning of the navigational guide 1, a plurality of contact members are provided, each of them being designed to match with a corresponding contact area on the patient's vertebra 100.

The plurality of contact members comprises a main contact member 11 intended to couple with a main contact area, corresponding to the spinous process 101 of the vertebra 100.

The main contact member 11 is located at the vertex of the V-shaped bridge 5.

The main contact member 11 defines a seat 12 that extends around the spinous process. The seat 12 is mainly defined by a pair of lateral walls 13 bridged together by an connecting structure 14. The arms 6 of the V-shaped bridge 5 depart from the external sides of said lateral walls 13.

According to the embodiment disclosed in FIGS. 1-7, the seat 12 is open in the cranial-caudal direction in order to avoid that the ligaments of the patients be severed before placing the guide in the coupling configuration (open profile).

As an alternative, not disclosed, the seat 12 can be closed in the cranial-caudal direction by walls connecting both sides of the lateral walls 13 forming a closed profile surrounding the spinous process 101 in order to ensure an excellent stability to the operative guide 1.

As an alternative, not disclosed, the seat 12 can be closed in the cranial or in the caudal direction by a wall in order to allow for a less invasive operative technique (semi-open profile).

The plurality of contact members comprises a pair of first auxiliary contact members 15, matching with first auxiliary contact areas, and a pair of second auxiliary contact members 16, matching with second auxiliary contact areas.

In the present embodiment, the first auxiliary contact areas correspond to the laminae 102 of the patient's vertebra 100.

In the present embodiment, the second auxiliary contact areas correspond to the facet 103. However, in alternative embodiments, the second auxiliary contact areas 16 can correspond to the transverse processes 104.

The two first auxiliary contact members 15, as well as the two second auxiliary contact members 16, are symmetrically positioned on the navigational guide 1, with respect to a median plane passing through the main contact member 11. However, depending on the patent anatomy a unsymmetrical arrangement is also possible.

The two second auxiliary contact members 16 are laterally placed with respect to the first auxiliary contact members 15; in other words, the first auxiliary contact members 15 are positioned between the main contact member 11 and the second auxiliary contact members 16.

In the present embodiment, each of the first auxiliary contact members 15 comprises a contact finger, projecting from the a respective tubular guiding member 2, near the distal opening 2b, downwards in respect to the V-shaped bridge 5. The free end of said contact fingers is designed with a shape matching with the laminae 102 of the patient's vertebra 100. It is noted that the contact finger extends from a caudal/inner portion of the tubular guiding member 2 and is directed toward the median plane and away from the vertex of the V-shaped bridge 5.

In the present embodiment, each of the second auxiliary contact members 16 comprises a contact finger, projecting from the tubular guiding member 2 near the distal opening 2b along the longitudinal direction of the tubular guiding member 2. The free end of said contact fingers are designed to match with the facet 103 of the patient's vertebra 100 or with the transverse processes 104.

Referring now to FIGS. 8-12, a second embodiment of a patient-specific navigational guide 1' for spinal surgery is illustrated, which is specifically designed for operations on a thoracic vertebra 100'.

The second embodiment shares most of the features of the first embodiment. Features which are identical or similar in structure or function are indeed identified with the same reference number in the attached drawings. In the following description, only the technical aspects substantially different from those of the first embodiment are explicitly addressed.

The patient-specific navigational guide 1' according to the second embodiment also comprises two tubular guiding members 2, integral with a bearing frame 3 with a V-shaped bridge 5 and a non-rectilinear bridge 8. Compared to the first embodiment, the V-shaped bridge 5 extends for a longer distance in the caudal direction, so as to reach the spinous process 101 which is farther from the vertebral body in thoracic vertebrae 100'.

In the depicted embodiment, the main contact member 11 has an open profile with no bottom wall; however, different configurations may be envisaged. In particular the main contact member 11 defines a seat 12 that extends around the spinous process. The seat 12 is mainly defined by a pair of lateral walls 13 bridged together by a flat connecting structure 14 and a curved connecting structure 14a.

In this second embodiment, the first auxiliary contact areas matching with the first auxiliary contact members 15 lie on the laminae 102 of the vertebra 100'; the second auxiliary contact areas matching with the second auxiliary contact members 16 correspond to the transverse processes 104 of the vertebra 100'. In this case the auxiliary contact members 16 comprise fingers 16a connected to the tubular guiding member 12 by means of connecting plates 16b.

Each of the first auxiliary contact members 15 comprises a contact finger extending from a caudal/inner portion of the tubular guiding members 2, near the distal opening 2a, and directed toward the median plane and toward the vertex of the V-shaped bridge 5.

The surgical procedure employing a patient-specific navigational guide 1, 1' comprises a pre-operative planning and an intra-operative procedure. The pre-operative planning comprises a first step of acquiring CT/MRI scans of the surgical site, a second step of reconstructing a three-dimensional image of the site and a third step of planning the screw placements (or the location of the cuts) on the three-dimensional image by means of computer-aided design tools.

Once the screw axes or the cutting planes have been identified, the steps of designing and producing the patient-specific navigational guide 1, 1' are performed.

The intra-operative procedure is described below with reference to the patient-specific guide 1.

The procedure comprises a step of cleaning the vertebra and cutting the ligaments (if necessary) and a subsequent step of coupling the guide to the cleansed vertebra. Note that, prior to the coupling, the correct location and alignment of the guiding members 2 can be checked on a real size three-dimensional model of the vertebra.

After the coupling, two awls are inserted into the tubular guiding members 2. After removal of the awls the surgeon can check the entry points for the pedicle screws. In the next step, the pedicle of the vertebra is opened with a probe or drill inserted in the guiding member 2. The surgeon can use a feeler to help himself in the process. Finally, after removing the probes or drills, the pedicle screws can be inserted via the tubular guiding members 2 by means of a screwdriver.

In an alternative method, the adapter sleeve is capped on top of the tubular guiding members 2 and two Kirchner wires are inserted into the vertebra instead of directly fixing the pedicle screws. After removal of the navigational guide, the Kirchner wires are used to guide the insertion of a cannulated pedicle screw.

Obviously a person skilled in the art, in order to meet specific needs, will readily acknowledge the possibility of changes and variations to the navigational guides described above, comprised within the scope of protection as defined by the following claims.

The invention claimed is:

1. A patient-specific navigational guide for use in spinal surgery, the guide comprising two tubular guiding members extending from a proximal opening and a distal opening for guiding a surgical operation on a patient's vertebra; the two tubular guiding members being integral with a bearing frame comprising at least five contact members designed to match with a corresponding plurality of contact areas on the patient's vertebra in order to define a unique coupling configuration of the patient-specific navigational guide on the patient's vertebra, wherein said contact members comprise a main contact member designed to couple with a main contact area of the plurality of contact areas corresponding to a spinous process of the patient's vertebra in said coupling configuration and at least one pair of first and second auxiliary contact members designed to abut on auxiliary contact areas of the plurality of contact areas respectively corresponding to a laminae of the patient's vertebra and to a facet or to a transverse process in said coupling configuration, wherein the bearing frame comprises a V-shaped bridge directly connecting the two tubular guiding members and a non-rectilinear bridge further connecting directly the two tubular guiding members at different circumferential proximal portions of the tubular guiding members near the proximal openings and at least one summit portion defining a more proximal portion of the navigational guide.

2. The patient-specific navigational guide according to claim 1, wherein the V-shaped bridge has two arms, each arm being connected to one of the tubular guiding members and pointing toward a caudal direction so that a vertex of the V-shaped bridge is positioned above the spinous process of a lumbar vertebra and defines said main contact member.

3. The patient-specific navigational guide according to claim 2, wherein each of the two arms has a shape defined by planar surfaces enlarging from the tubular guiding member to the vertex.

4. The patient-specific navigational guide according to claim 3, wherein each arm comprises a proximal surface and a distal surface, each having a substantially triangular shape, and two opposite planar surfaces each having a substantially rectangular shape.

5. The patient-specific navigational guide according to claim 4, wherein a width (L) of the two opposite planar surfaces of each arm defines an extended connecting portion between the tubular guiding members and the V-shaped bridge, preferably the width (L) being greater than half the distance (A) between the proximal opening and the distal opening.

6. The patient-specific navigational guide according to claim 1, wherein the V-shaped bridge connects the two tubular guiding members at a substantially central portion of each tubular guiding members, between the proximal opening and the distal opening.

7. The patient-specific navigational guide according to claim 1, wherein considering an inner volume defined by the two tubular guiding elements and the V-shaped bridge, the non-rectilinear bridge extends from the proximal portions of the tubular guiding members towards an outside.

8. The patient-specific navigational guide according to claim 1, wherein the non-rectilinear bridge comprises two arms connected by a curved portion defining the summit portion.

9. The patient-specific navigational guide according to claim 1, wherein the non-rectilinear bridge remains within a theoretical plate comprising the two tubular guiding members.

10. The patient-specific navigational guide according to claim 1, wherein the non-rectilinear bridge and the V-shaped bridge are arranged to form an angle of at least 90° between a theoretical plate comprising the non-rectilinear bridge and the two tubular guiding members and a theoretical plate comprising the V-shaped bridge.

11. The patient-specific navigational guide according to claim 1, wherein the non-rectilinear bridge with the summit portion lies on a plane comprising longitudinal axes of the tubular guiding members.

12. The patient-specific navigational guide according to claim 1, wherein the guiding members present diameters within a range of 3 mm and 18 mm.

13. The patient-specific navigational guide according to claim 12 wherein the guiding members present diameters within a range of 3 mm and 9 mm.

14. A patient-specific navigational guide for use in spinal surgery, the guide comprising two tubular guiding members extending from a proximal opening and a distal opening for guiding a surgical operation on a patient's vertebra; the two tubular guiding members being integral with a bearing frame comprising at least five contact members designed to match with a corresponding plurality of contact areas on the patient's vertebra in order to define a unique coupling configuration of the patient-specific navigational guide on the patient's vertebra, wherein said contact members comprise a main contact member designed to couple with a main contact area of the plurality of contact areas corresponding to a spinous process of the patient's vertebra in said coupling configuration and at least one pair of first and second auxiliary contact members designed to abut on auxiliary contact areas of the plurality of contact areas respectively corresponding to a laminae of the patient's vertebra and to a facet or to a transverse processes in said coupling configuration, wherein the bearing frame comprises a V-shaped bridge connecting the two tubular guiding members and a non-rectilinear bridge further connecting directly the two tubular guiding members at proximal portions of the tubular guiding members near the proximal openings and at least one summit portion defining a more proximal portion of the navigational guide; and wherein the non-rectilinear bridge with the summit portion lies on a plane comprising longitudinal axes of the tubular guiding members.

\* \* \* \* \*